(12) United States Patent
Orbay et al.

(10) Patent No.: US 11,406,507 B2
(45) Date of Patent: *Aug. 9, 2022

(54) TOTAL WRIST PROSTHESIS AND RELATED METHODS

(71) Applicant: SKELETAL HOLDINGS, LLC, Miami, FL (US)

(72) Inventors: Jorge L. Orbay, Miami, FL (US); Edward J. Tremols, Miami, FL (US); Brian A. Cooke, Miami, FL (US)

(73) Assignee: SKELETAL HOLDINGS, LLC, Miami, FL (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/566,160

(22) Filed: Sep. 10, 2019

(65) Prior Publication Data

US 2020/0000602 A1 Jan. 2, 2020

Related U.S. Application Data

(63) Continuation of application No. 15/468,223, filed on Mar. 24, 2017, now Pat. No. 10,413,418.

(Continued)

(51) Int. Cl.
*A61F 2/42* (2006.01)
*A61B 17/17* (2006.01)
(Continued)

(52) U.S. Cl.
CPC ........ *A61F 2/4261* (2013.01); *A61B 17/1686* (2013.01); *A61B 17/1782* (2016.11);
(Continued)

(58) Field of Classification Search
CPC .......... A61F 2/4261–2002/4297; A61F 2/4606
See application file for complete search history.

(56) References Cited

U.S. PATENT DOCUMENTS 4,040,130 A * 8/1977 Laure .................... A61F 2/4261
623/21.13
4,106,128 A * 8/1978 Greenwald ........... A61F 2/3804
623/21.13

(Continued)

FOREIGN PATENT DOCUMENTS

DE 29500476 8/1995
EP 0532440 3/1993
(Continued)

OTHER PUBLICATIONS

Patent Cooperation Treaty (PCT) Written Opinion and Search Report Dated Jul. 24, 2017.

(Continued)

*Primary Examiner* — Alvin J Stewart
(74) *Attorney, Agent, or Firm* — Lott & Fischer, P.L.

(57) ABSTRACT

Disclosed is a wrist prosthesis, and methods for implanting same, the prosthesis comprising radial component having two sides, the first side comprising a stem and the second side comprising a concave dish; a carpal component having two sides, the first side comprising a stem, and the second side comprising a ball end, the ball end being connected to the carpal component through a neck, the neck being narrower than the diameter of the ball end; and a lunate component having two sides, the first side comprising a cavity adapted to receive said carpal component's ball end, and the second side comprising a convex surface adapted to engage said radial component's concave dish.

17 Claims, 18 Drawing Sheets

Related U.S. Application Data

(60) Provisional application No. 62/312,869, filed on Mar. 24, 2016.

(51) Int. Cl.

| | |
|---|---|
| *A61B 17/16* | (2006.01) |
| *A61F 2/30* | (2006.01) |
| *A61F 2/46* | (2006.01) |
| *A61B 17/86* | (2006.01) |
| *A61B 17/90* | (2006.01) |
| *A61B 17/88* | (2006.01) |

(52) U.S. Cl.
CPC ...... *A61F 2/30734* (2013.01); *A61F 2/30749* (2013.01); *A61F 2/30771* (2013.01); *A61F 2/4606* (2013.01); *A61B 17/1604* (2013.01); *A61B 17/86* (2013.01); *A61B 17/8897* (2013.01); *A61B 17/90* (2021.08); *A61F 2002/30518* (2013.01); *A61F 2002/30604* (2013.01); *A61F 2002/30616* (2013.01); *A61F 2002/30654* (2013.01); *A61F 2002/30663* (2013.01); *A61F 2002/30774* (2013.01); *A61F 2002/30785* (2013.01); *A61F 2002/30878* (2013.01); *A61F 2002/30881* (2013.01); *A61F 2002/30884* (2013.01); *A61F 2002/30892* (2013.01); *A61F 2002/4264* (2013.01); *A61F 2002/4292* (2013.01); *A61F 2002/4658* (2013.01); *A61F 2002/4687* (2013.01); *A61F 2310/00407* (2013.01)

(56) References Cited

U.S. PATENT DOCUMENTS

| | | | | |
|---|---|---|---|---|
| 4,678,472 A | * | 7/1987 | Noiles | A61F 2/32 |
| | | | | 623/23.4 |
| 4,950,299 A | | 8/1990 | Noiles | |
| 5,314,485 A | * | 5/1994 | Judet | A61F 2/4261 |
| | | | | 623/21.13 |
| 5,507,821 A | | 4/1996 | Sennwald et al. | |
| 6,168,630 B1 | | 1/2001 | Keller et al. | |
| 7,160,329 B2 | * | 1/2007 | Cooney, III | A61F 2/3804 |
| | | | | 623/20.11 |
| 7,625,408 B2 | * | 12/2009 | Gupta | A61F 2/4261 |
| | | | | 623/21.11 |
| 7,628,819 B2 | | 12/2009 | Gupta et al. | |
| 8,052,757 B1 | * | 11/2011 | Scheker | A61F 2/4261 |
| | | | | 623/21.13 |
| 8,118,876 B2 | | 2/2012 | Gupta et al. | |
| 8,333,806 B2 | | 12/2012 | Scheker | |
| 8,562,689 B2 | * | 10/2013 | Scheker | A61F 2/4261 |
| | | | | 623/21.13 |
| 8,641,770 B2 | * | 2/2014 | Scheker | A61F 2/4261 |
| | | | | 623/21.16 |
| 8,758,445 B2 | | 6/2014 | Gupta et al. | |
| 9,078,758 B2 | * | 7/2015 | Leibel | A61F 2/4261 |
| 9,119,642 B2 | | 9/2015 | Burstein et al. | |
| 9,233,004 B2 | | 1/2016 | Gupta et al. | |
| 9,962,261 B1 | | 5/2018 | Scheker | |
| 10,413,418 B2 | * | 9/2019 | Orbay | A61F 2/30734 |
| 2003/0187511 A1 | * | 10/2003 | Ball | A61F 2/4261 |
| | | | | 623/21.13 |
| 2003/0216813 A1 | * | 11/2003 | Ball | A61F 2/4261 |
| | | | | 623/21.12 |
| 2006/0030946 A1 | | 2/2006 | Ball et al. | |
| 2006/0161260 A1 | * | 7/2006 | Thomas | A61F 2/4261 |
| | | | | 623/21.12 |
| 2008/0051909 A1 | | 2/2008 | Wolfe et al. | |
| 2009/0240336 A1 | * | 9/2009 | Vander Meulen | A61F 2/3804 |
| | | | | 623/18.11 |
| 2013/0090738 A1 | | 4/2013 | Linares et al. | |
| 2014/0288660 A1 | | 9/2014 | Gupta et al. | |
| 2015/0100132 A1 | | 4/2015 | Vanasse et al. | |
| 2017/0258597 A1 | | 9/2017 | Deutchman et al. | |
| 2018/0168814 A1 | | 6/2018 | Scheker | |

FOREIGN PATENT DOCUMENTS

| | | |
|---|---|---|
| EP | 2460492 | 6/2012 |
| FR | 2661817 | 11/1991 |
| WO | WO2015137809 | 9/2015 |

OTHER PUBLICATIONS

European Supplemental Examination Report for EP 17771212 dated Mar. 14, 2019.

De Martino, et al.—"Dual Mobility Cups in Total Hip Arthroplasty"—World Journal of Orthopedics—Jul. 18, 2014—Anniversary Special Issue—5(3): 180-187.

"MWPIII Total Wrist Prosthesis—Surgical Technique" Zimmer GmbH—2010—Switzerland.

Heffernan, et al.—"Development and Validation of a Novel Modular Dual Mobility Hip Bearing"—ORS—2011 Annual Meeting.

* cited by examiner

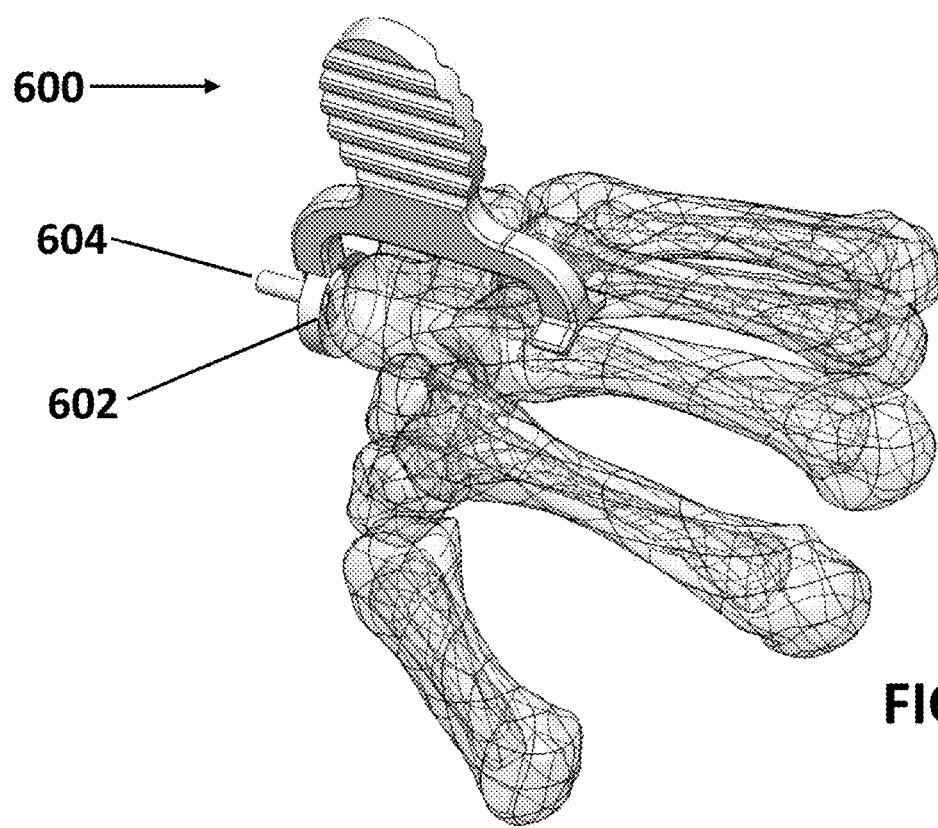
FIG. 22
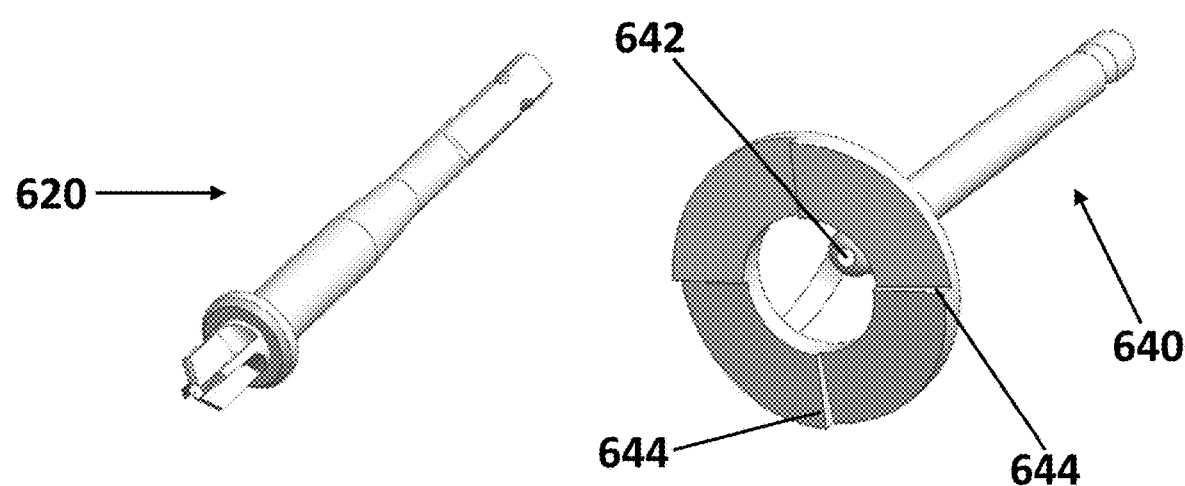
FIG. 23
FIG. 24

TOTAL WRIST PROSTHESIS AND RELATED METHODS

CLAIM OF PRIORITY

This application is a continuation of U.S. patent application Ser. No. 15/468,223 filed Mar. 24, 2017, now U.S. Pat. No. 10,413,418, which claims the benefit of U.S. Provisional Patent Application Ser. No. 62/312,869 filed on Mar. 4, 2016, the contents of which are incorporated herein by reference.

FIELD OF INVENTION

The invention relates generally to prosthetic implants and in particular to prosthetic implants for use in a total wrist replacement procedure.

BACKGROUND OF THE INVENTION

As shown in FIG. 1, the human wrist consists of a cluster of 8 small bones, the carpal bones, which flexibly connect the metacarpal bones 15, 16, 17, 18, 19), located in the palm, with the ulna (3) and radius (4) located in the forearm. The carpal bones are generally arranged into distal and proximal rows (5,6). The distal row of carpal bones consists of the trapezium (7) trapezoid (8), capitate (9) and hamate (10) bones. The proximal row of carpal bones consists of the scaphoid (11), lunate (12), triquetrum (13), and pisiform (14) bones. In normal operation of a healthy wrist, the articular surface of the radius (15) provides a concave bearing surface which supports the articulation of the scaphoid (11) and lunate (12) as the wrist goes through its range of motion.

Due to injury, degenerative changes, disease (such as arthritis) or other conditions, a person may experience pain, discomfort, or difficulty when operating the wrist through its range of motion. Known procedures for such wrist conditions are to fuse the scaphoid (11) and lunate (12) bones (and possibly other carpal bones) to themselves in a "four corner" fusion, or, in more extreme cases, total wrist arthrodesis, which fuses the radius, some of the carpal bones and one of the metacarpal hones. While these procedures alleviate pain and discomfort, they greatly restrict the range of motion of the wrist resulting in quality of life issues for the patient by limiting the utility of the wrist. In addition, in certain circumstances, because the bones in question are too deteriorated, or, in the case of fractures, not available, fusion is not possible.

In such circumstances, an available treatment is to replace all or some of the carpal bones with a prosthetic wrist in a procedure commonly referred to as a total wrist replacement Although previous efforts have been made to develop prosthetic wrists, they have met often with disappointing results. Presently available wrist prostheses provide too limited a range of motion, dislocate too easily, place too much stress on bones resulting in failure or fractures, cause complications such as infections, and wear prematurely requiring additional surgeries during the patient's lifetime, among other flaws. In addition, the methods presently used for implanting such prosthetic wrists often result in poorly aligned joints and poor joint performance.

Accordingly, there is a need in the art for a prosthetic wrist, and associated methods for implanting same, which provides a patient with a range of motion that approximates that of a healthy wrist, is long-lasting, provides adequate support for the remaining hand and forearm bones, and avoids many of the drawbacks of existing prosthetic wrists.

SUMMARY OF THE INVENTION

A wrist prosthesis used in a total wrist replacement is disclosed. The wrist prosthesis of the present invention replaces the proximal row of carpal bones and restores wrist function using three separate components—a carpal component, a lunate component, and a radial component. When assembled, the prosthesis attaches to the radius in the forearm and to the trapezoid (optionally), capitate, hamate (optionally), and third metacarpal bones in the hand. The three components of the prostheses, when assembled provide for a wide range of movement between the radial and carpal components.

The radial component of the wrist prosthesis comprises a stem at its proximal end for insertion into and attachment to the radius, and an approximately semi-spherical concave bearing surface, or "dish", at its distal end for engaging the lunate component. The carpal component of the wrist prosthesis comprises a stem and an alignment pin at its distal end for attachment to the capitate and third metacarpal bones, and a ball end at its proximal end for engaging the lunate component. Some embodiments of the present invention additionally include holes for attachment of the carpal component to the trapezoidal and/or hamate bones.

Interposed between the radial and carpal components is the lunate component which is comprised, in in its radial-facing side, of a semi-sphere which closely matches the geometry of the dish of the radial component. The carpal-facing side of the lunate component is comprised of a cavity that closely matches the geometry of the ball end of the carpal component and allows the lunate component to "snap" onto the ball end of the carpal component. The center of the ball-shaped cavity in the lunate component is slightly offset proximally relative to the center of the outer spherical surface of the lunate component in order to provide a "self-centering" characteristic to the arrangement of components as discussed in greater detail below.

The lunate component is manufactured from a durable yet resilient material, such as ultra-high-molecular-weight polyethylene ("UHMWPE"). The carpal and radial components are manufactured from a high quality surgical-grade metallic alloy such as Cobalt-Chromium-Molybdenum ("CoCrMo") well known for biomedical applications such as joint replacements. The use of a polyethylene lunate component in cooperation with the CoCrMo carpal and radial components provides various benefits, including (a) avoidance of any metal-on-metal interfaces between moving parts and known complications thereof; (b) self-lubrication of the internal and external interfaces of the lunate component; (c) dampening and absorption of impact loads on the prosthesis; and (d) exceptional durability.

Also disclosed is a method for performing a total wrist replacement using the wrist prosthesis of the present invention. The method includes making an incision in the dorsal side of the wrist and exposing the carpal bones and the articular surface of the radius. Next, the proximal row of carpal bones, namely the scaphoid, lunate, triquetrum, and pisiform bones, are excised. An insertion hole, is next drilled in the articular surface of the radius, optionally using a radial alignment tool, and the stem of the radial component is inserted through the insertion hole into the radius. Optionally, the articular surface of the radius may be prepared using a specialized shaping tool prior to insertion of the radial component.

Two holes are next drilled, optionally using a carpal alignment tool; the first, longitudinally through the capitate bone and into the third metacarpal bone to receive the stem of the carpal component, and the second into the central aspect of the capitate to receive the alignment pin of the carpal component. Optionally, the capitate bone may be resized and prepared using a specialized shaping tool prior to insertion of the stem and alignment pin of the carpal component into the capitate and third metacarpal bones. Optionally, the carpal component be also attached to the hamate and trapezoidal bones through screws inserted into attachment holes in some embodiments of the carpal component.

The carpal-facing cavity end of the lunate component is next "snapped" onto the ball end of the carpal component and the radial-facing end of the lunate component is buttressed against the dish end of the radial component where it is allowed to "float." Once all of the components are manipulated into correct alignment to permit a range of motion approximating that of a natural wrist, the incision is closed.

Although the invention is illustrated and described herein as embodied in a wrist prosthesis, it is nevertheless not intended to be limited to only the details shown, since various modifications and structural changes may be made therein without departing from the spirit of the invention and within the scope and range of equivalents of the claims. Moreover, many of the principles and techniques discussed in the following description can be applied to prostheses used in other joints in the human anatomy such as the elbow, shoulder, hip, knee or ankle.

The construction of the invention, together with additional objects and advantages thereof will be best understood from the following description of the specific disclosed embodiments when read in connection with the accompanying drawings.

BRIEF DESCRIPTION OF THE DRAWINGS

FIG. 22 is an orthographic view of a capitate long axis guide in accordance with the present invention.

FIG. 23 is an orthographic view of a stop reamer and planer in accordance with the present invention.

FIG. 24 is an orthographic view of a capitate shaper in accordance with the present invention.

DETAILED DESCRIPTION OF THE INVENTION

Figure 1:
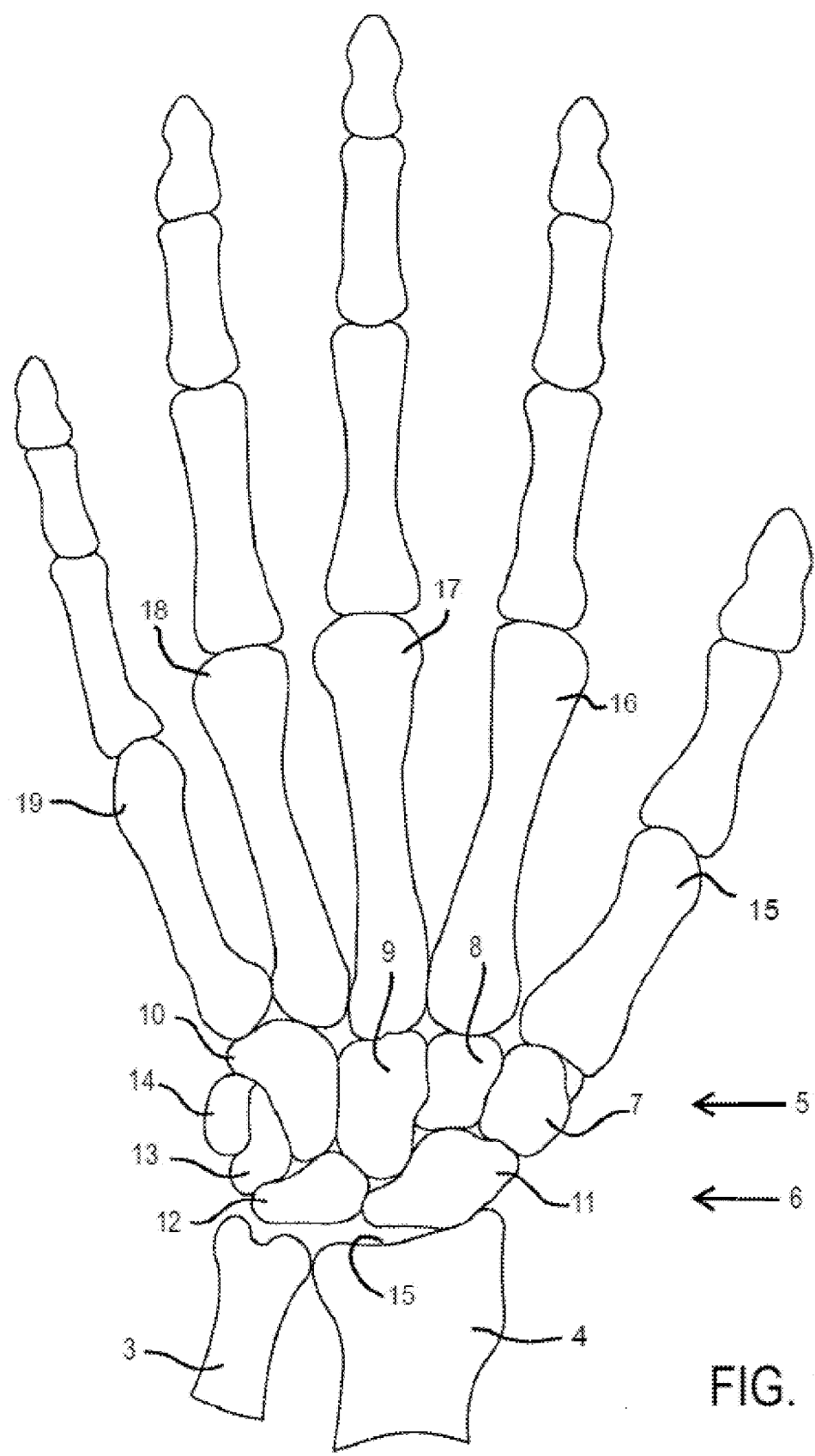
FIG. 1 is an illustration of the bones of the human hand provided for reference only and known in the prior art.
Figure 2:
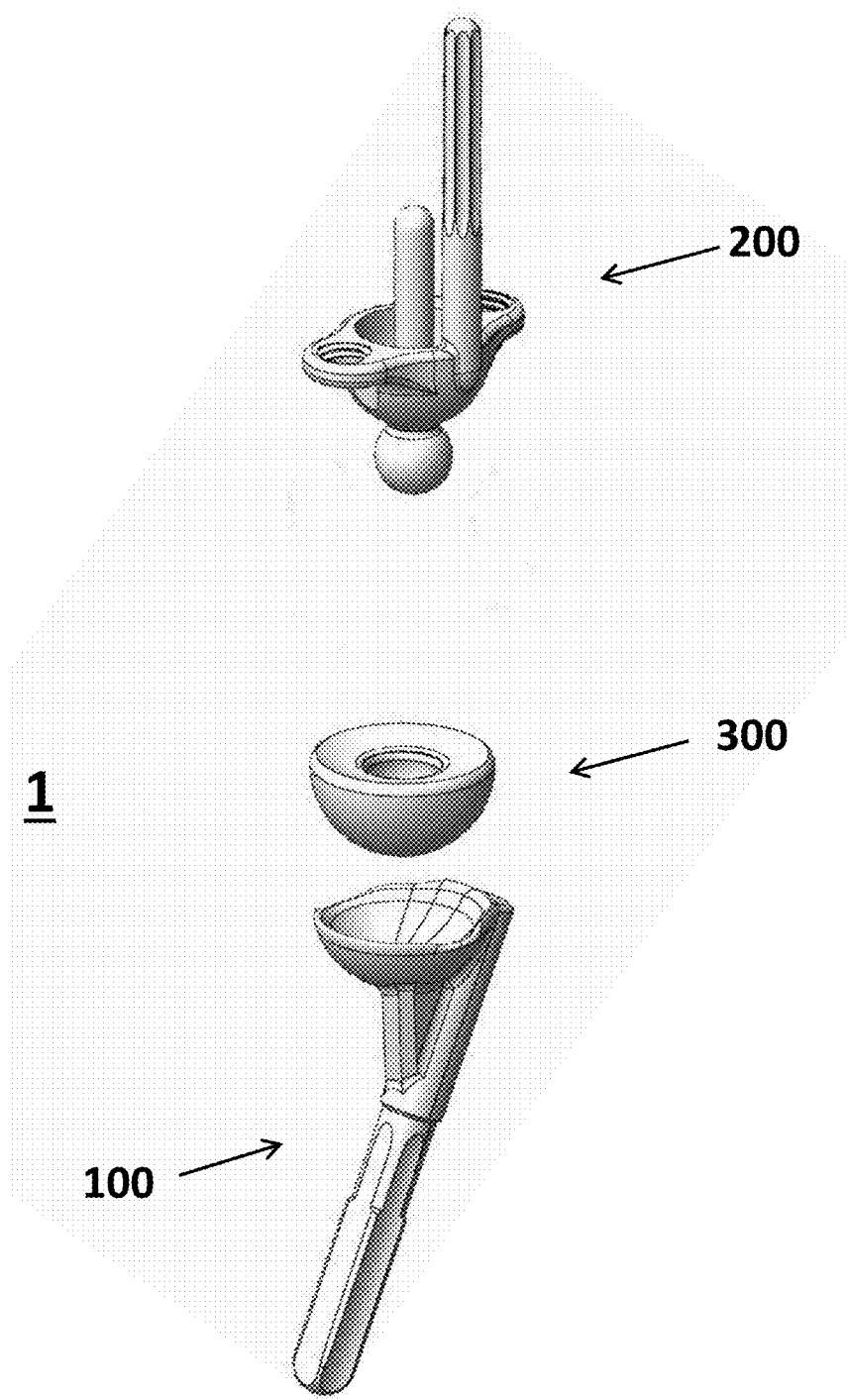
FIG. 2 is an exploded orthographic view of the dorsal aspect of the radial, carpal and lunate components of a wrist prosthesis according to the present invention.
Figure 3:
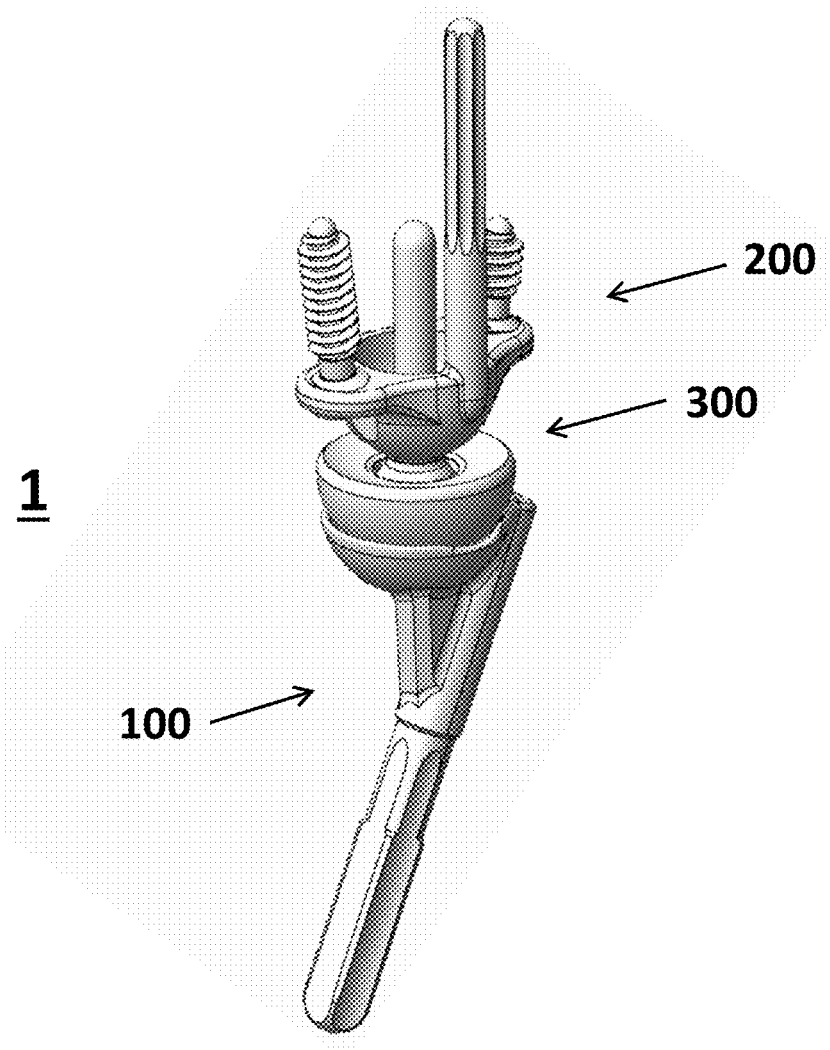
FIG. 3 is an assembled view of the dorsal aspect of the radial, carpal and lunate components of a wrist prosthesis according to the present invention.

FIG. 2 is an exploded orthographic view of the three components of a wrist prosthesis (1) according to the present invention. As shown, the lunate component (300) is interposed between the radial component (100) and the carpal component (200). FIG. 3 shows an assembled view of the three components from the same perspective.

Figure 4:
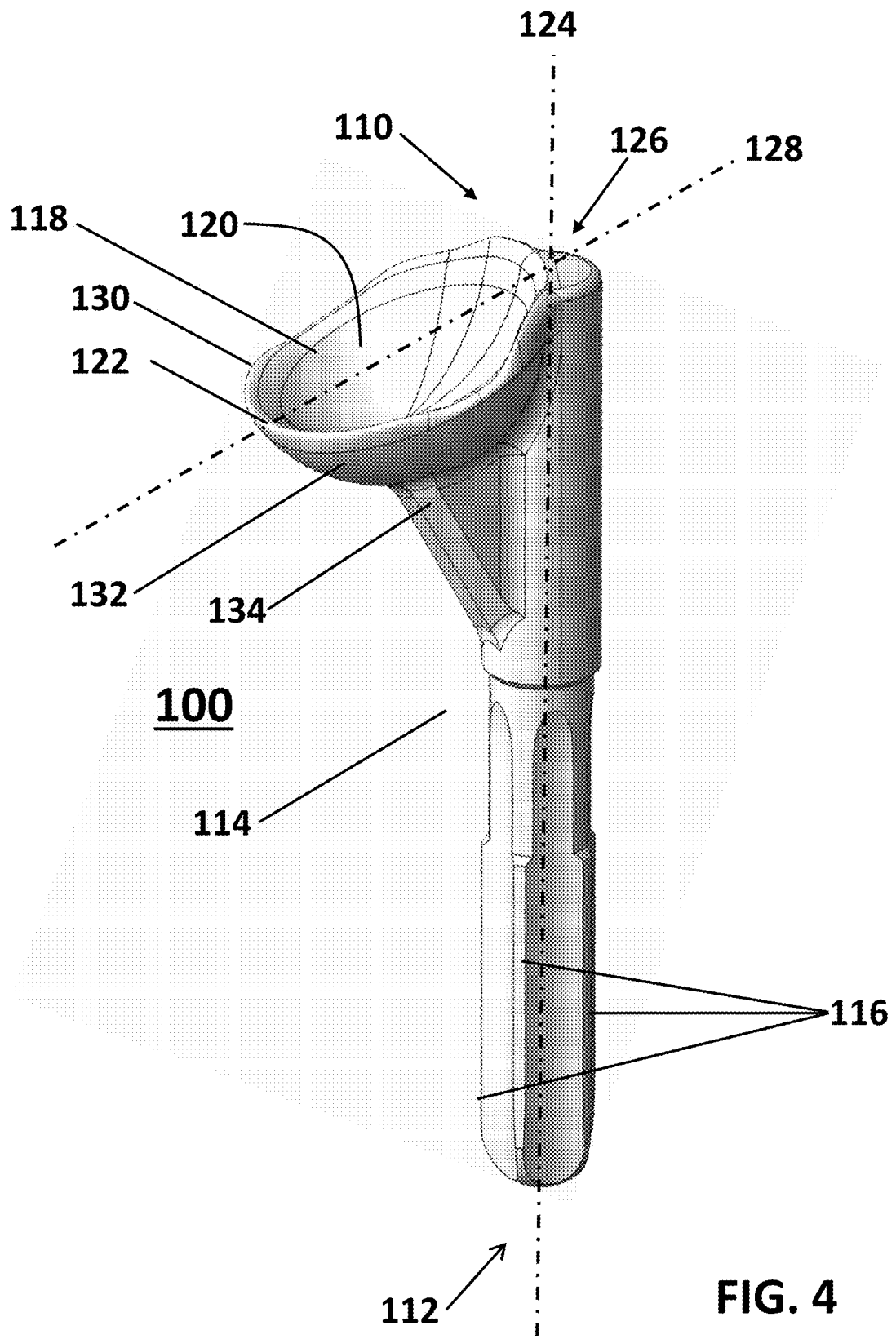
FIG. 4 is an orthographic distal end view of the radial component of wrist prosthesis according to the present invention.
Figure 5:
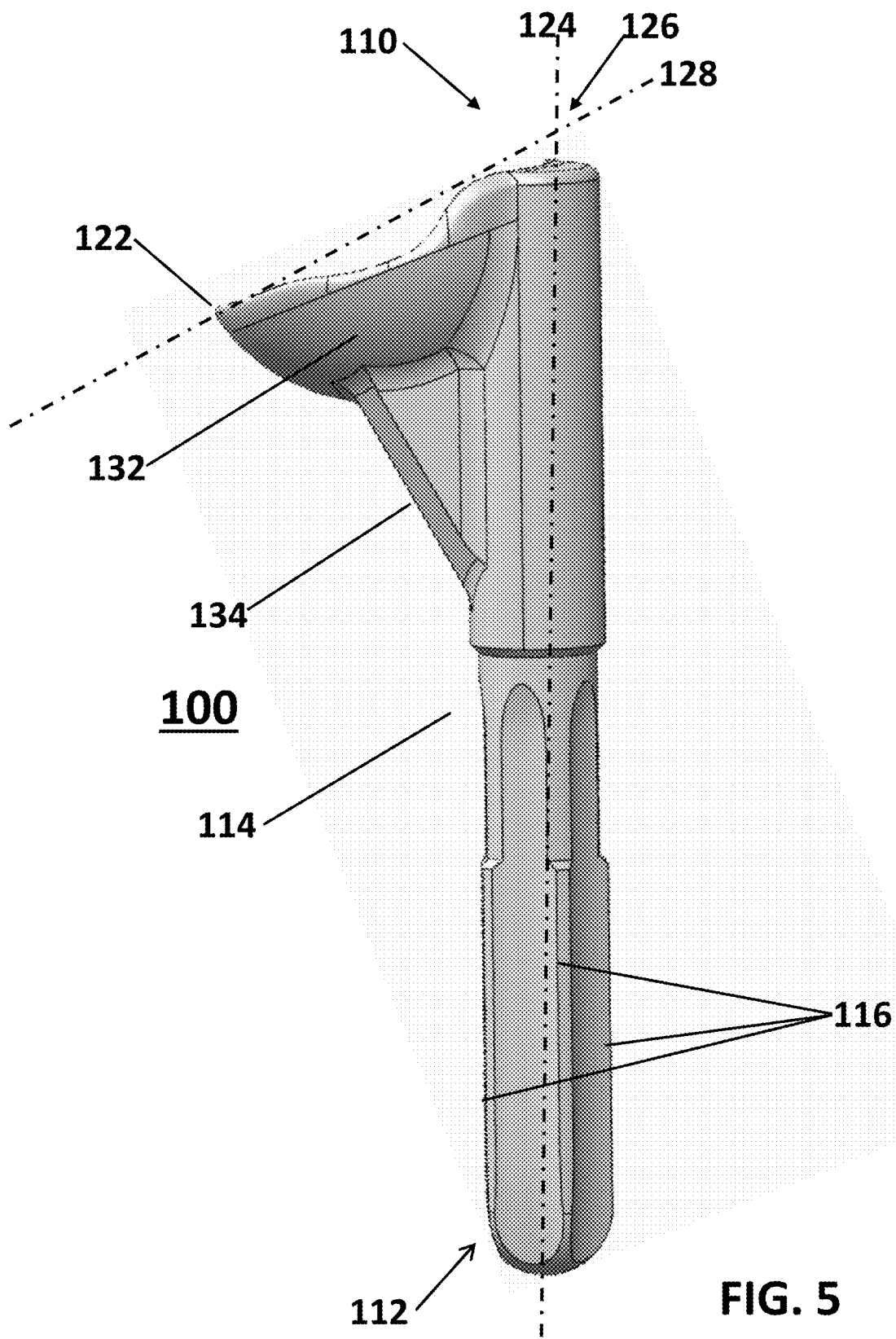
FIG. 5 is a side view of the radial component of a wrist prosthesis according to the present invention.
Figure 6:
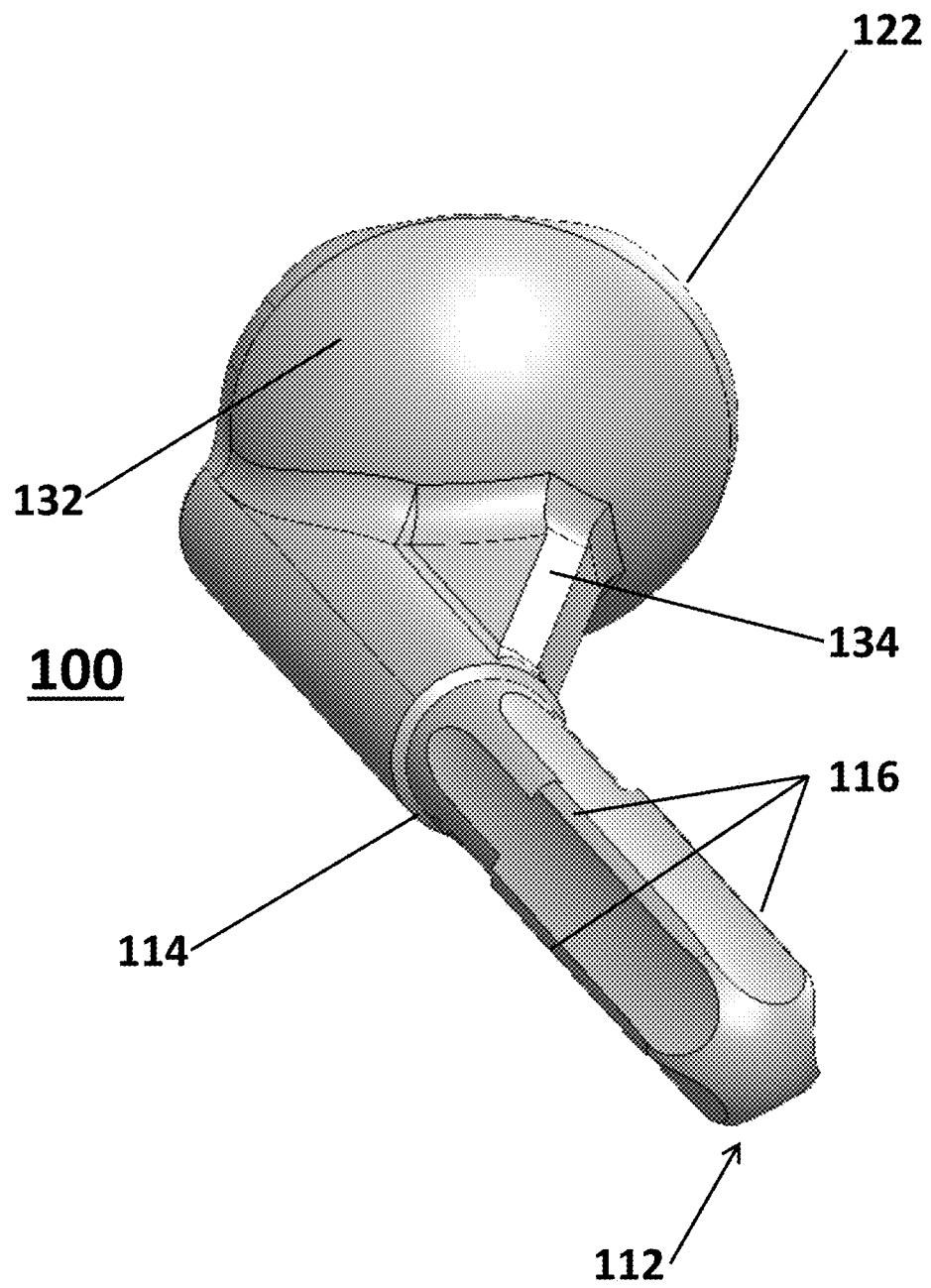
FIG. 6 is a proximal end view of the radial component of a wrist prosthesis according to the present invention.

Referring next to FIG. 4, shown is an orthographic representation of a radial component (100) according to the present invention. FIGS. 5 and 6 respectively provide side and proximal end views of the radial component (100) and illustrate all details thereof. As shown in FIG. 4, the radial component (100) is comprised of a proximal end (112) and a distal end (110). Stem (114) is projected in the direction of the proximal end and is adapted for insertion through the articular face of the radius and for penetration into the medullary canal of the radius. The stem of the radial component may optionally include flutes (116) and/or a roughened surface finish, such as titanium plasma spray ("TPS") coating, to promote post-operative bone growth for more permanent fixation after healing, and to prevent rotation of the component in the bone. The distal end of the radial component provides a distally facing concave dish (118) which is adapted to receive the convex portion (301) (shown in FIGS. 10, 11, 12 and 13) of the lunate component (300) upon assembly of the prosthesis, as described in detail below.

The internal surface (120) of dish (118) is a substantially spherically concave section which closely matches the geometry of the convex portion of the lunate component (300). In some embodiments of the radial component (100), the spherical section defined by the internal surface (120) of dish (118) is less than half of a full sphere. The dish optionally includes one or more lip extensions (122) which provide additional rotational support area for the lunate component (300) which could be beneficial to provide for maximum flexing of the assembled prosthesis without dislocation of the lunate component (300).

To provide optimal alignment between the various components and the surrounding anatomy, stem (112) is arranged with respect to dish (118) so that the longitudinal axis (124) of stem (114) forms an angle (126) of between approximately 60 and 80 degrees with respect to an imaginary line (128) coplanar with the edge (130) of dish (118). In addition, stem (114) is offset laterally with respect to the center of dish (118) so that longitudinal axis (124) of the stem (114) intersects the internal surface (120) of dish (118) approximately tangentially. The external, bone contacting, surface (132) of dish (118) can optionally be, spherical or other shape that conforms to the articular face of the radius bone.

An additional optimal feature of radial component (100) is keel (134) which buttresses the junction between stem (114) and dish (118). In addition to providing structural support to dish (118), keel (134) minimizes the possibility of radial component (100) rotating about longitudinal axis (124) after insertion into the radius. Furthermore, keel (134) acts as a wedge creating a tighter fit between the radius bone and stem (114). Keel (134) may have a sharp edge to facilitate penetration into the radius bone. Additionally, keel (134) may be of solid construction (as shown) or may be hollow, to provide a dual edge for penetration of the radius bone and allows bone material to become wedged in the inner space of keel (134).

Radial component (100), in one embodiment of the present invention, is manufactured from a high quality surgical-grade metallic alloy, such as CoCrMo well known for biomedical applications such as joint replacements. However, titanium or other metallic or non-metallic materials are also suitable for this component in alternative embodiments.

Figure 7:
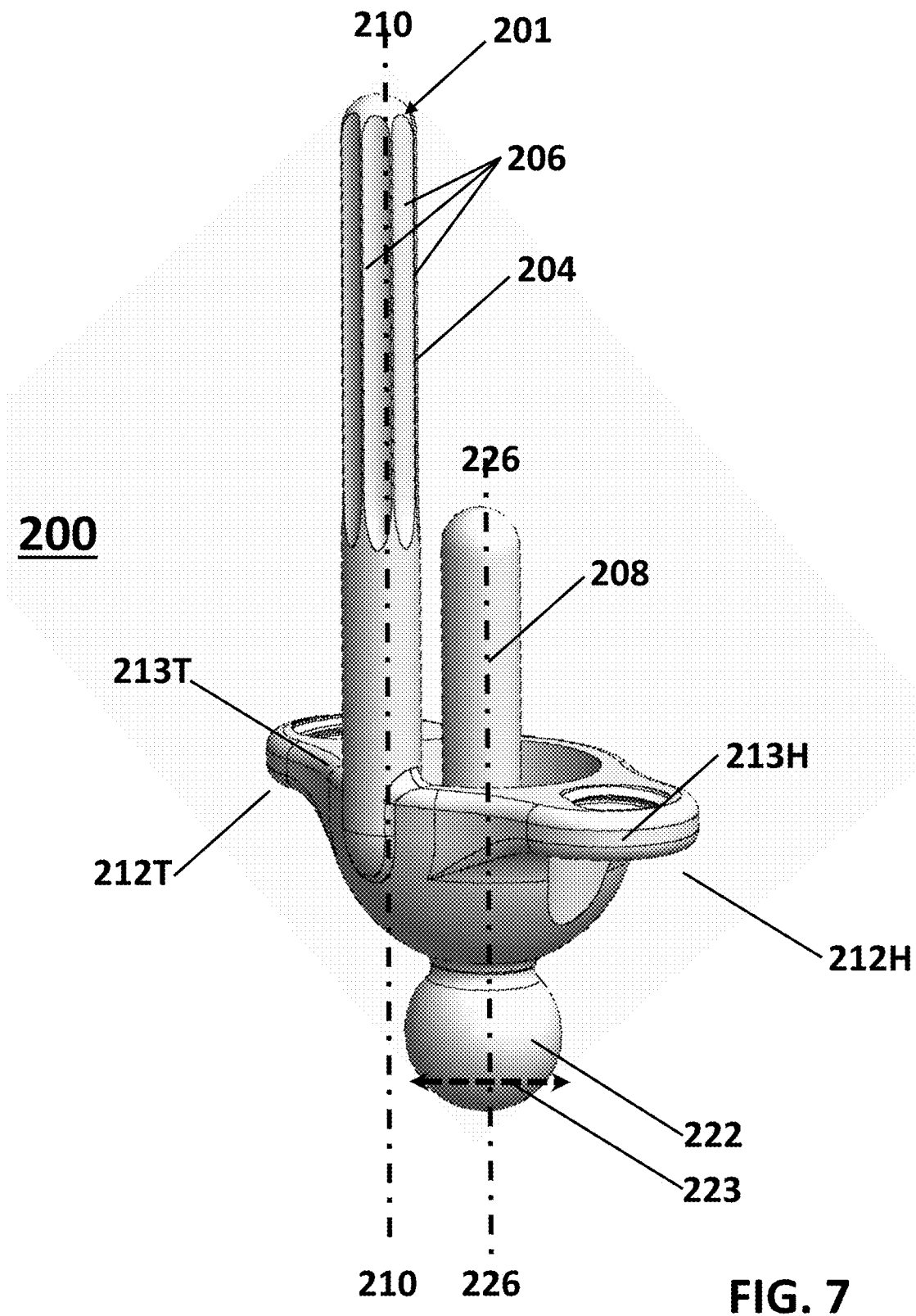
FIG. 7 is an orthographic view from the dorsal side of the carpal component of a wrist prosthesis according to the present invention which, optionally, includes two wings and attachment holes for the hamate and trapezoidal bones.
Figure 8:
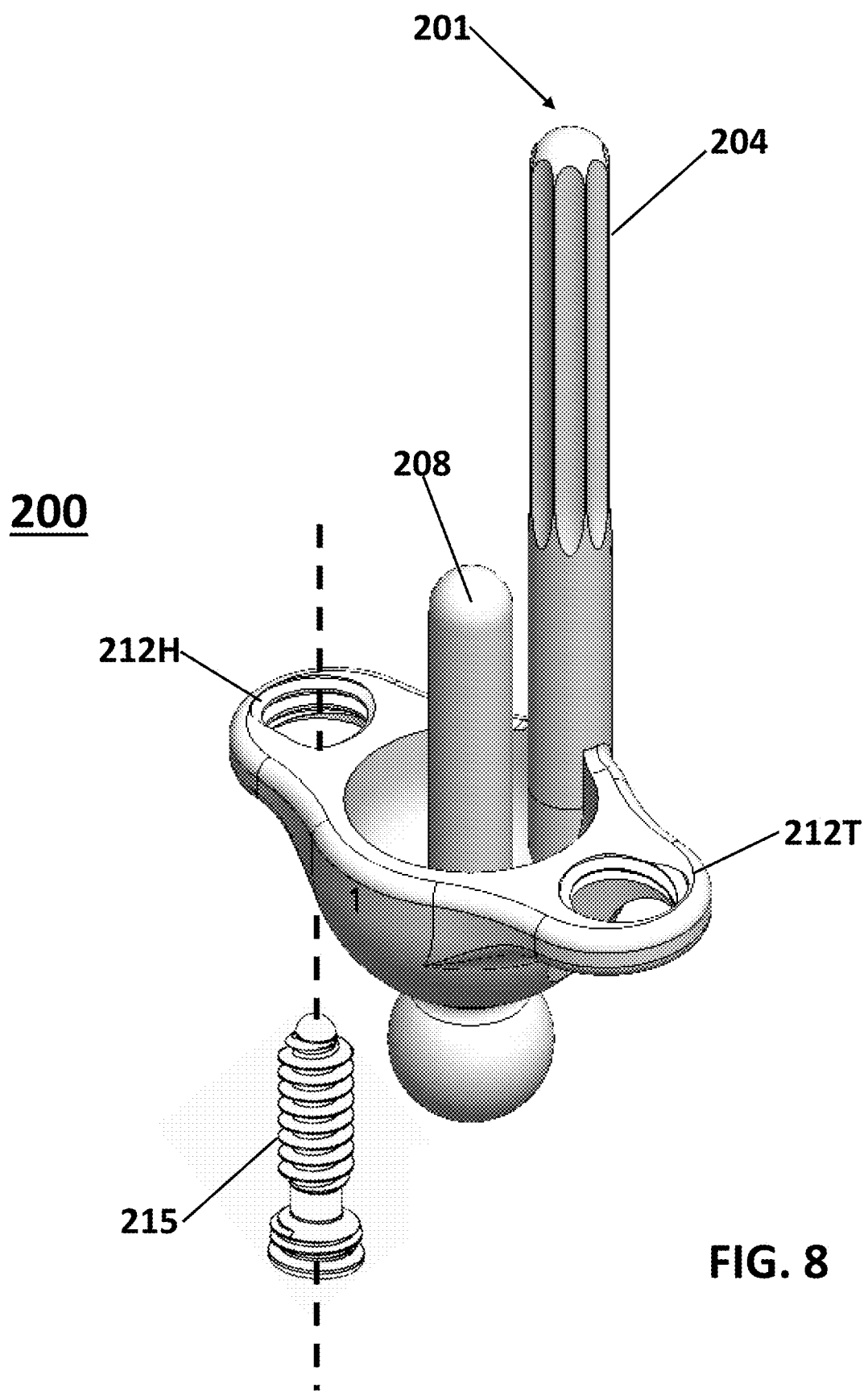
FIG. 8 is an orthographic view from the palmar side of the carpal component of a wrist prosthesis according to the present invention.

Referring next to FIG. 7, shown is an orthographic representation of a carpal component (200) according to the present invention. FIG. 8 shows a side view of the carpal component (200) and FIG. 9 shows a cross section of the carpal component (200).

With reference to FIG. 7, the distal end (201) of the carpal component (200) is comprised of a stem (204) which is adapted to penetrate into the third metacarpal bone, preferably into the medullary canal of the third metacarpal bone. The stem of the carpal component may optionally include flutes (206) and/or a roughened surface finish to promote post-operative bone growth for more permanent fixation after healing, and to prevent rotation of the component in the bone. The carpal component also comprises alignment pin (208), in generally parallel alignment with stem (204), which is adapted to penetrate into the central aspect of the capitate bone. The purpose of alignment pin (208) is to minimize the possibility of rotation of carpal component (200) about longitudinal axis (210) of stem (204) after implantation. Carpal component. (200) may also, optionally, include one or more wings (212T) (212H) which are positioned for anatomical alignment with the trapezoid (8) and hamate (10) bones and provide additional buttressing support for carpal component (200) against said bones. Wings (212T), (212H) may optionally also include fastener holes (213T), (213H) for securing wings (212T) (212H) to the trapezoid (8) and hamate (10) bones using fasteners ((215) in FIG. 9.

Figure 9:
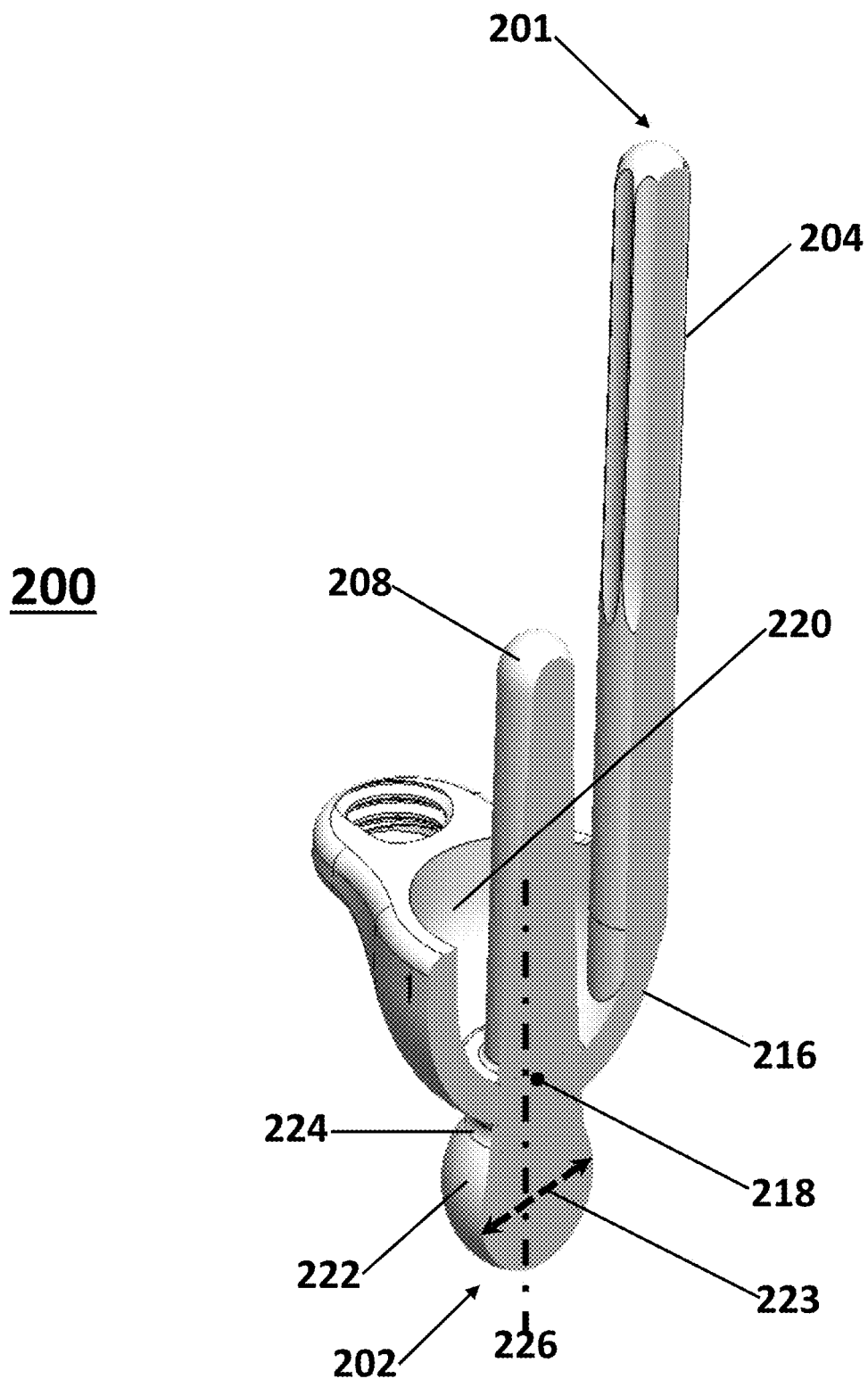
FIG. 9 is an orthographic cross-sectional view of the carpal component of a wrist prosthesis of FIG. 8 according to the present invention.

As best observed in FIG. 9, the stem (204) and alignment pin (208) of the carpal component terminate in cap (216) which is a concave structure with respect to distal, end (202) of the carpal component. Alignment pin (208) terminates at or near the center (218) of the internal surface (220) of cap (216), while stem (204) is offset dorsally with respect to alignment pin (208) and terminates at the edge of cap (216). The internal surface (220) of cap (216) is adapted to contact, and optionally encapsulate, the capitate bone upon implantation into the patient's hand.

The proximal end (202) of carpal component (200) comprises ball end (222) with a diameter (223) which is connected to cap (216) through neck region (224). Ball end (222) is a semi-complete (between 70% and 97% in the disclosed embodiment but in any event greater than 50% of a sphere) sphere with its center in substantially direct longitudinal alignment with the center of cap (216) and the longitudinal axis (226) of alignment pin (208). The ball end (222) and neck region (224) closely complement the geometry of corresponding features in the lunate component (300) as discussed in more detail below.

Like radial component (100), carpal component (200), in one embodiment of the present invention, is manufactured from a high quality surgical-grade metallic alloy such as "CoCrMo" well known for biomedical applications such as joint replacements. However, titanium or other metallic or non-metallic materials may also be suitable for this component.

Figure 10:
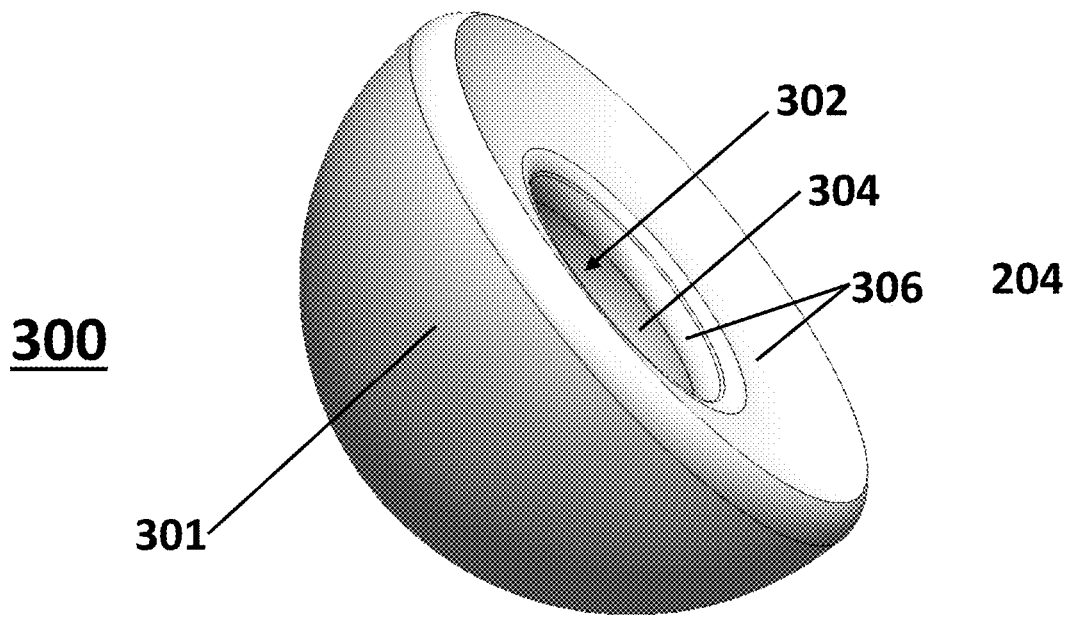
FIG. 10 is an orthographic view of the lunate component of a wrist prosthesis according to the present invention.
Figure 11:
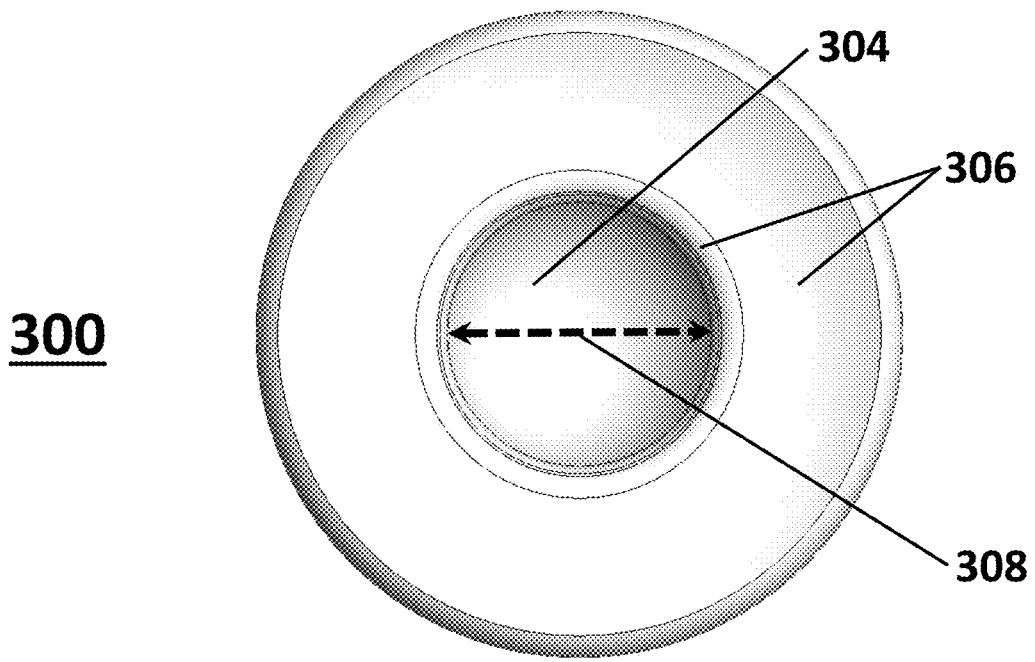
FIG. 11 is a top view of the lunate component of a wrist prosthesis according to the present invention.
Figure 12:
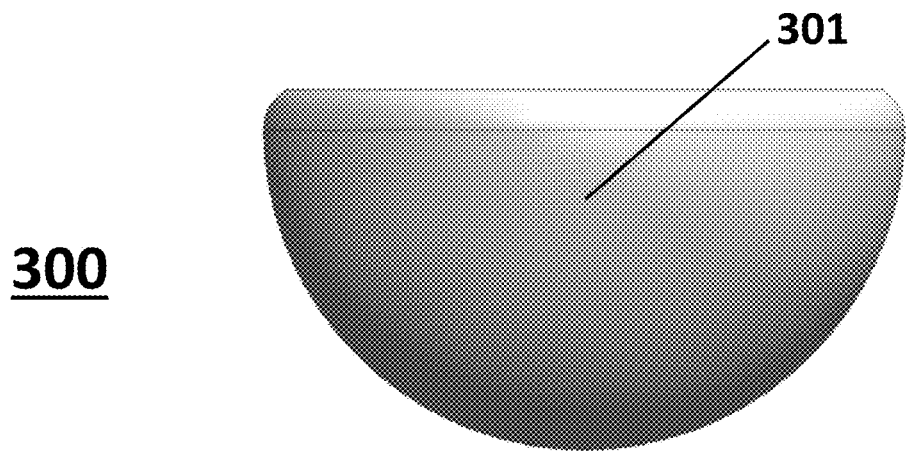
FIG. 12 is a side view of the lunate component of a wrist prosthesis according to the present invention.
Figure 13:
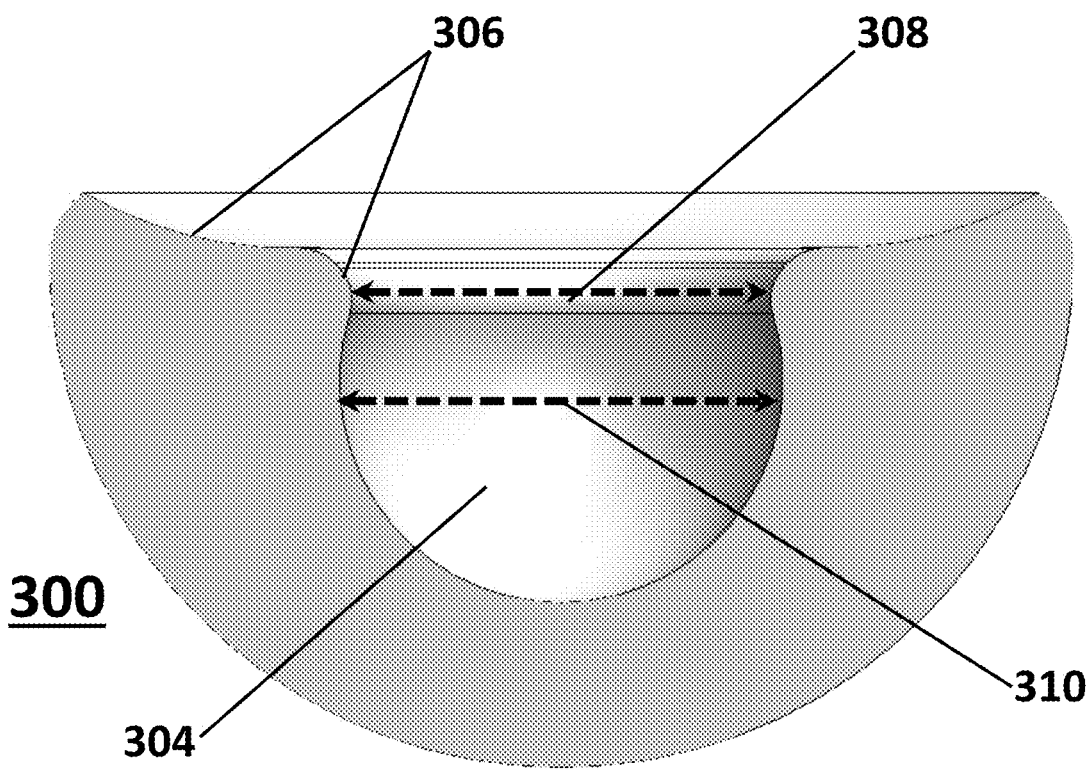
FIG. 13 is a cross-sectional view of the lunate component of a wrist prosthesis according to the present invention.

Referring next to FIG. 10, shown is an orthographic representation of a lunate component (300) according, to the present invention. FIGS. 11 and 12 illustrate, respectively, top and side views of the lunate component (300). FIG. 13 is a cross sectional view, enlarged for clarity, of the lunate component (300) which, as evident from all views, is radially symmetrical.

As shown in FIGS. 10-13, the external surface (301) of lunate component (300), which is adapted to interface with the internal surface (120) of dish (118) of radial component (100) (see FIGS. 4-6), approximately defines a half-sphere. However, alternative embodiments need not necessarily define a half-sphere. Alternative embodiments of lunate component (300) could define an external surface that is greater than half of a sphere, or smaller than half of a sphere, it being understood that the greater the external surface is, the lower the possibility will be of dislocation of the lunate component (300) with respect to radial component (100).

Referring now to FIG. 10 through FIG. 13, lunate component (300) includes a cavity (302) comprised of a spherical region (304) and a shoulder region (306). The spherical region (304) of cavity (302) in all embodiments comprises more than a half-sphere so that the diameter of the "mouth" (308) of the spherical region (304) is narrower than the diameter (310) of the spherical region (304) and also narrower than the diameter (223) of ball end (222) of carpal component (200). Also, the diameter (310) of the spherical region (304) is somewhat larger than the diameter (223) of the ball end (222) of carpal component (200) as to provide sufficient clearance for the ball end of the carpal component to rotate freely within the spherical region (304). The shoulder region (306), in turn, gradually widens away from the spherical region (304) to form a funnel-like toroidal structure atop the lunate component. The spherical and shoulder regions of cavity (302) closely match the geometry of the ball end (222) and neck region (224) of carpal component (200) (See FIGS. 7-9).

Lunate component (300) is manufactured from a durable yet resilient material, such as "UHMWPE", or other surgical grade resilient material.

Figure 14:
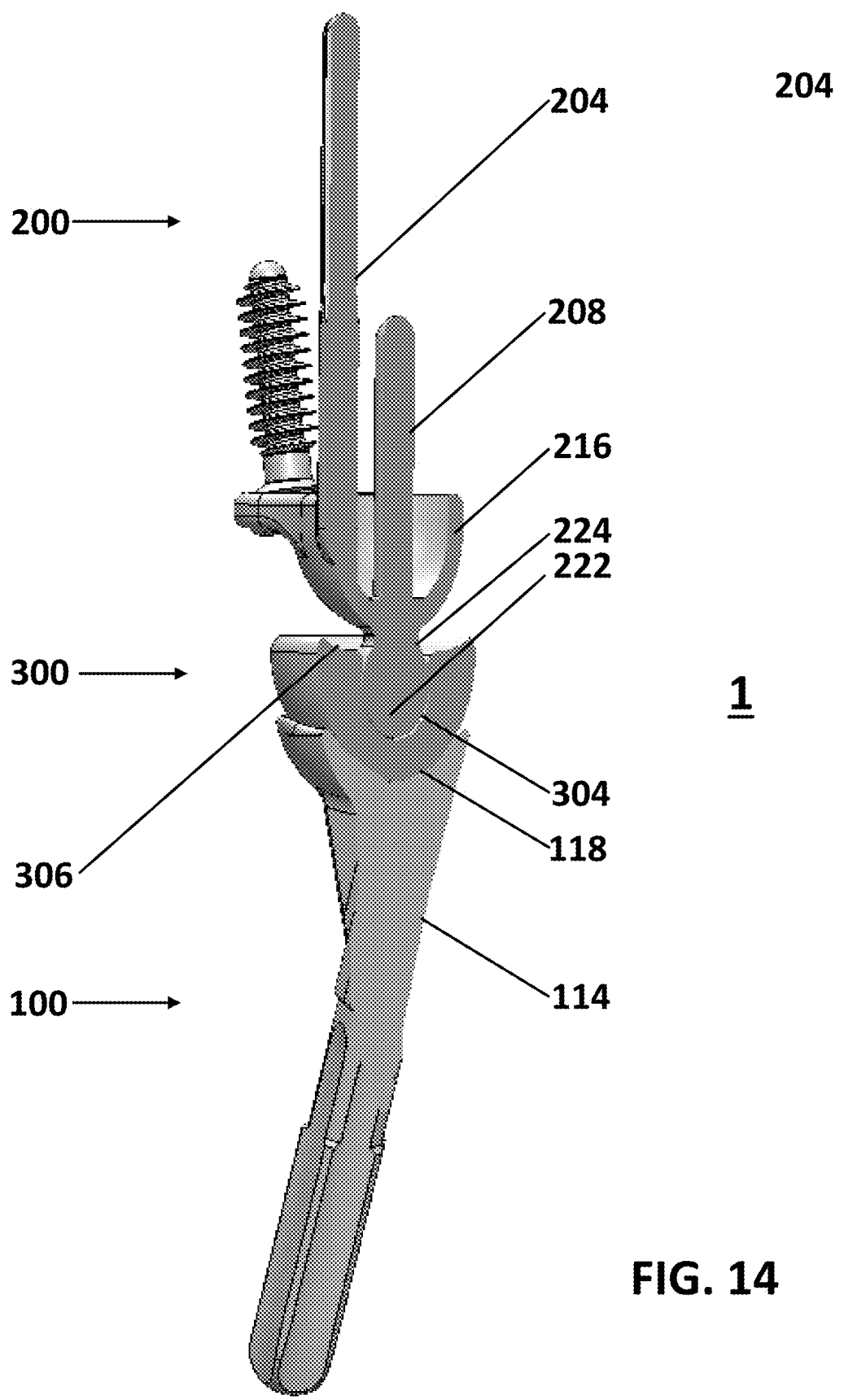
FIG. 14 is a cross-sectional assembled view of the carpal, lunate, and radial components of a wrist prosthesis according to the present invention.
Figure 15:
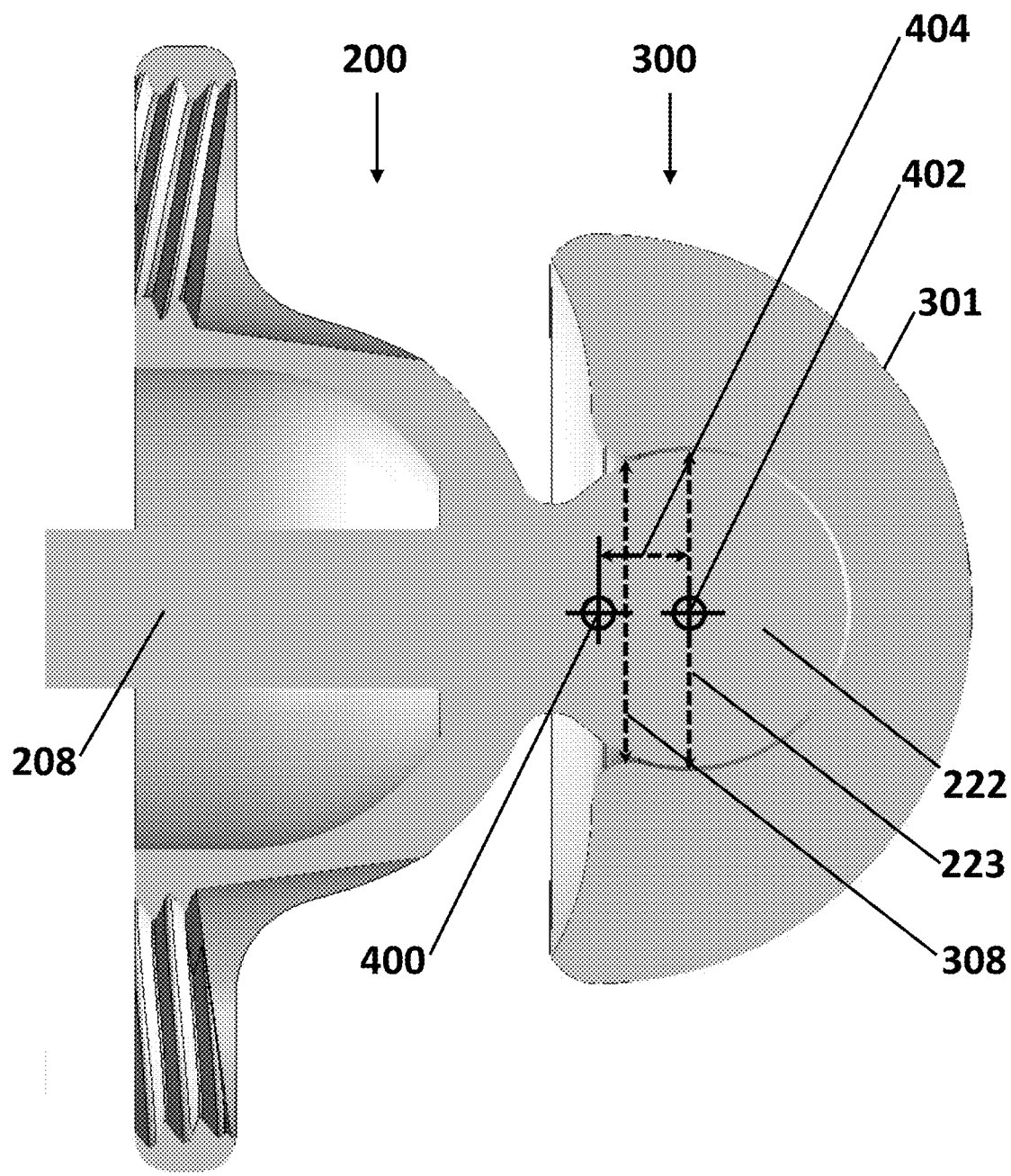
FIG. 15 is a detail of a cross-sectional view of the assembled lunate and carpal components of a wrist prosthesis according to the present invention.

Referring next to FIG. 14 and FIG. 15 therein are shown cross-sectional views of the carpal (200), lunate (300) and radial (100) components of the wrist prosthesis (1) of the present invention, upon assembly. As will be noted, since the mouth (308) of spherical region (304) of cavity (302) of the lunate component (300) is narrower than the diameter (223) of the ball end (222) of the carpal component (200), in order to assemble the carpal and lunate components, ball end (222) must be forced into cavity (302) until it snaps into place. That is, the lunate component is briefly deformed but immediately snaps back to its original shape retaining the ball end (222) within its cavity (302). Once in place, however, the lunate component is held securely with respect to the carpal component but the two components freely rotate and swivel with respect to each other.

Shown in FIG. 15 is a detail of the cross sectional view of the assembled lunate component (300) and carpal component (200). As is shown in this view, the center (402) of ball end (222) and the center (400) of the external surface (301) of the lunate component (300) are not coincident. Instead the center (402) of ball end (222) is offset proximally relative to the center (400) of the external surface (301) in the proximal-distal direction by a distance (404) of between 1 and 10 mm. This offset achieves two objectives. First, it minimizes the chance of the lunate and carpal components accidentally separating. By embedding cavity (302) deeper into the lunate component (300), the leverage caused at the limits of flexion will not cause the ball end to be dislodged. Second, the offsets provides the lunate-carpal coupling self-centering characteristics which ensure that through a series of flexions of the prosthesis the lunate component will be urged towards its neutral position, instead of remaining in an extreme position.

The self-centering characteristic of the lunate component is due to the fact that when the center (402) of the ball end (222) is offset proximally with respect to the center (400) of external surface (301) of the lunate component, the moment imparted on the lunate component by the natural normal load forces on the wrist is always greater, and in the center-biased direction, than the moment imparted on the lunate component by rotational frictional forces, which is non-centering. The greater the offset distance (404) between the two centers (400, 402), the greater the imbalance between the two moments and the stronger the self-centering tendency.

Referring again to FIG. 14, the lunate component (300), "floats" on top of the dish (118) of the radial component (100) and similarly freely rotates and swivels about the center of the dish (118). The two separate rotational pairings (carpal-lunate and lunate-radial) are independent of each other providing exceptional freedom of movement and flexibility in the prosthesis. Moreover, the interface between the UHMWPE and CoCrMo is naturally self-lubricating and provides exceptional smoothness and comfort in rotational and swiveling motions. It is noted, however, that the frictional torque between the lunate component (300) and the dish (118) of the radial component (100) is greater than the frictional torque between the ball end (222) of the carpal component (200) and the lunate component (300). Therefore, rotation will occur primarily in the carpal-lunate interface. Lunate-radial rotation will generally occur after a limit of rotation has been reached in the carpal-lunate interface, such as when the neck region (224) of the carpal component (200) comes into contact with the shoulder region (306) of the lunate component (300).

Figure 16A:
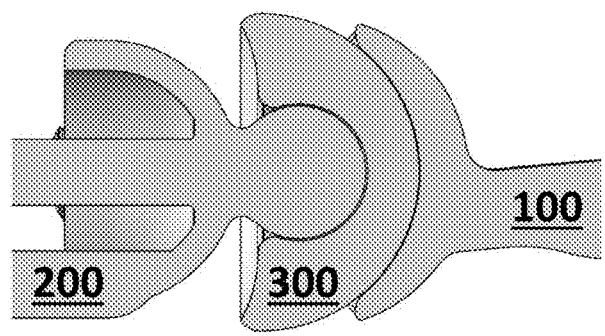
FIGS. 16A, 16B, and 16C are a sequence of views of the carpal, lunate and radial components illustrating their relative motion through an exemplary range of motion of a wrist prosthesis according to the present invention.
Figure 16B:
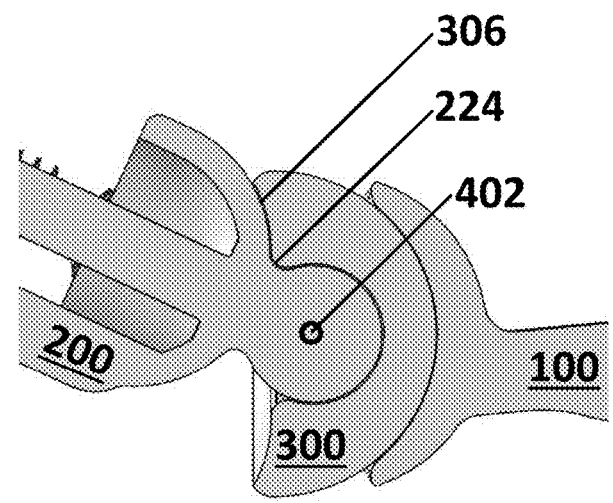
Figure 16C:
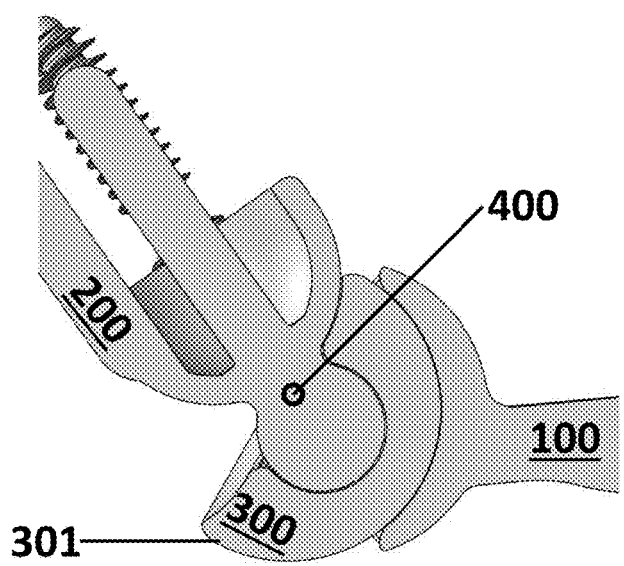

Shown in FIGS. 16A, 16B, and 16C is an exemplary sequence of relative movements between the carpal, lunate and radial components. Beginning with FIG. 16A, the carpal (200), lunate (300) and radial (100) components are in a neutral position. As upward force "F" is applied to the carpal component (200), the carpal component begins to rotate in a clockwise direction with respect to the lunate component (300). Because the frictional torque between the carpal and lunate components (200, 300) is less than that between the lunate and radial components (300, 100), there will be very little, if any, relative motion between the lunate (300) and radial (100) components at this phase.

This movement continues until, as shown in FIG. 16B, neck region (224) of the carpal component (200) comes into contact with shoulder region (306) of the lunate component (300). At this point, if upward force F continues to be applied to carpal component (200), the carpal and lunate components will begin to rotate together relative to the radial component (100) in a clockwise direction about the center (400) of the of the external surface (301) of the lunate component (300) as shown in FIG. 16C.

If a downward force is applied at this point to carpal component (200), a similar sequence (not shown) will be repeated in the opposite direction with relative counterclockwise motion first occurring between the carpal and lunate components (200, 300) until a limit of motion is reached and then with the carpal and lunate components (200, 300) moving in tandem in the counterclockwise direction relative to the radial component (100).

Figure 17:
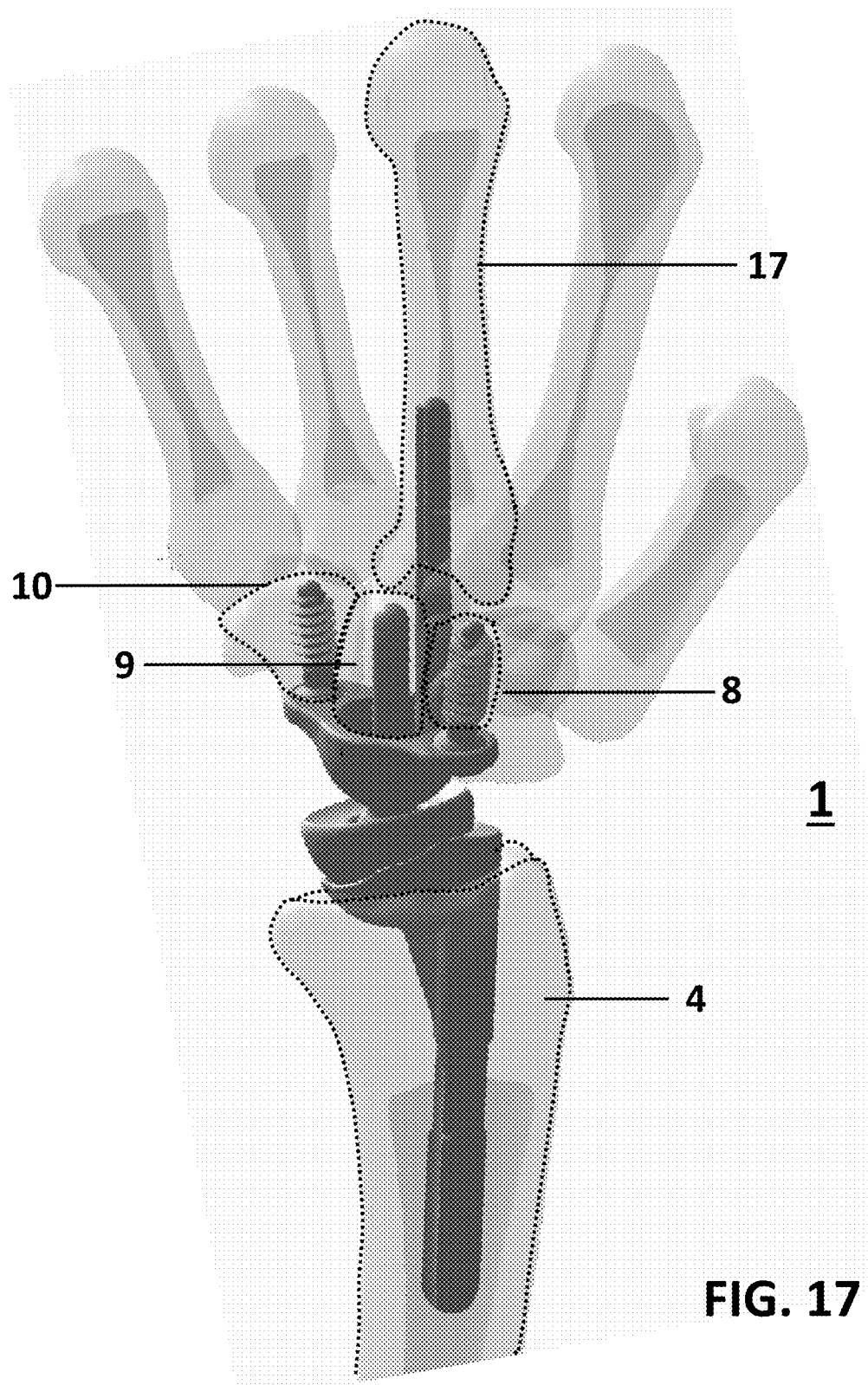
FIG. 17 illustrates an embodiment of the wrist prosthesis of the present invention implanted on a human hand with the surrounding skeletal anatomy represented as semi-transparent structures, shown for reference only.

Illustrated in FIG. 17 is an embodiment of the disclosed wrist prosthesis (1) shown with the surrounding skeletal anatomy for reference. Shown in dotted contour and transparent for clarity are the bones wherein the wrist prosthesis is implanted: The radius (4) the third metacarpal (17), the trapezoid (8), the lunate (9) and the hamate (10). The proximal row of carpal bones, namely the scaphoid, lunate, triquetrum, and pisiform bones are not shown, having been excised surgically as further explained below.

In addition to the above-disclosed prosthetic wrist, a method for surgically implanting same on a human patient is disclosed. The method includes the following basic sequence of steps:

An incision is made longitudinally on the dorsal side of the affected wrist and skin, muscle and tendons are retracted to expose the carpal bones and the distal end of the radius, including its articular surface.

The proximal row of carpal bones, namely the scaphoid, lunate, triquetrum, and pisiform bones, are excised, exposing the proximal articular surface of the second row of carpal bones, primarily the capitate and hamate bones.

Each of the lunate (300), carpal (200) and radial (100) components are optionally provided in one or more, sizes. The proper size of each component is dictated by the patient's anatomy. Optionally, this proper sizing may be accomplished during surgery by selecting and pre-assembling various sizes of equivalent modeling versions (not shown) of each of those components.

Figure 18:
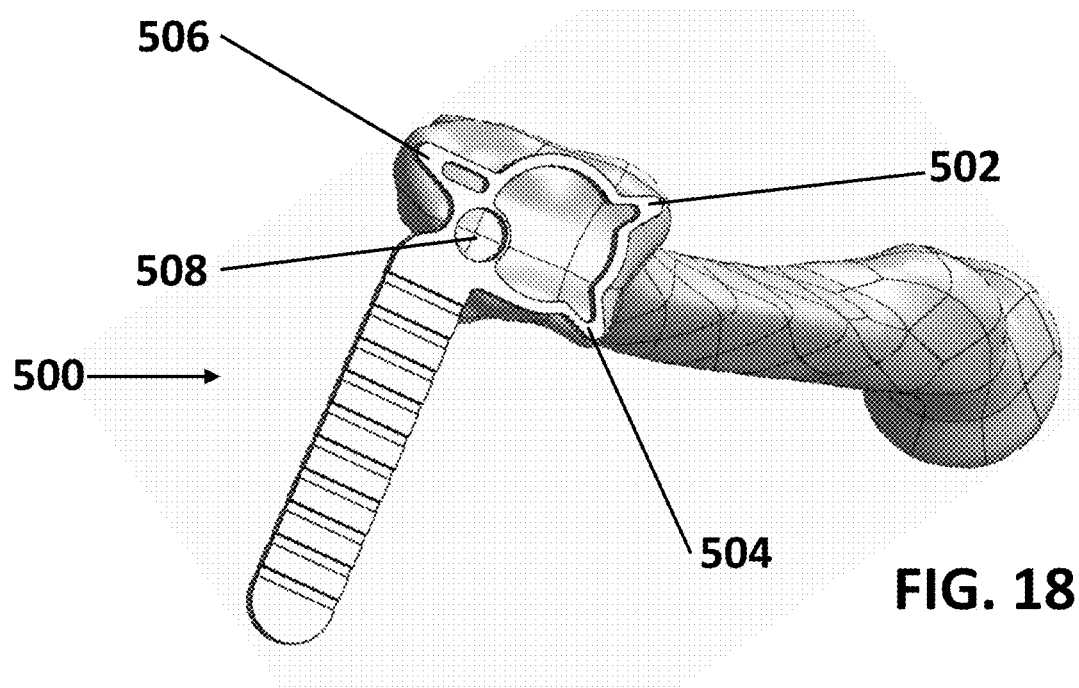
FIG. 18 is an orthographic view of a radial drilling guide alignment tool in accordance with the present invention.

An insertion hole is drilled near the center of the articular surface of the distal radius, optionally using a radial sizing/alignment tool for precise location of the hole. The optional radial sizing/alignment tool (500) is shown in FIG. 18. The radial sizing/alignment tool (500) includes visual cues (502, 504, 506) which can be matched—to the palmar and dorsal corners of the radio-ulnar joint, and the tip of the radial styloid, on the articular surface of the distal radius. Once the tool is properly placed, the center of circle (508) marks the spot where the radius should be drilled to insert the stem (114) of the radial component (100). The drilled hole is then reamed to the proper size.

Figure 19:
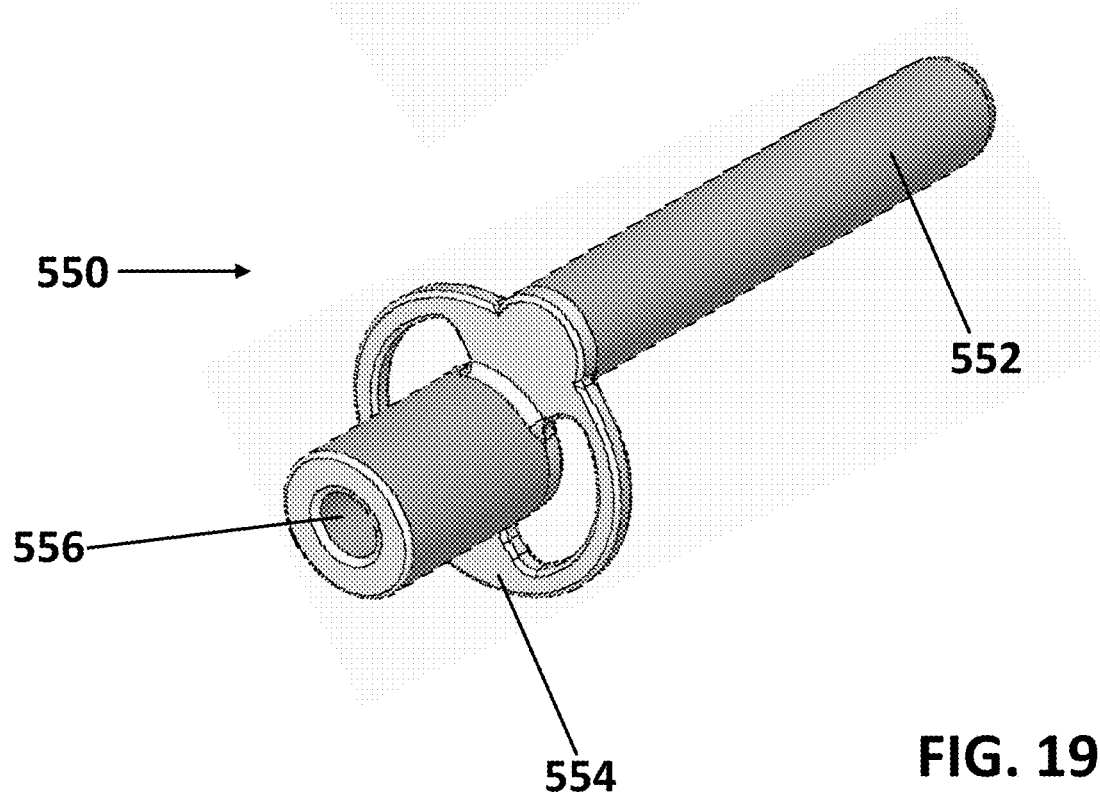
FIG. 19 is an orthographic view of a radial dish guide tool in accordance with the present invention.

The stem (114) of the radial component (100) is then inserted through the previously drilled hole into the radius until the leading tip of keel (134) contacts the articular surface. The precise orientation of the radial component (100) may be optimized prior to insertion by using an optional radial dish guide tool (550) shown in FIG. 19. The stem (552) of the radial dish guide tool (550) is inserted into the hole drilled into the articular surface of the radius and is then rotated until the outer edge of ring (55) is centered on the articular surface of the radius. A k-wire (not shown) is then inserted through orifice (556) and the radial dish guide tool (550) is removed. The location of the k-wire marks the center of dish (118).

Figure 20:
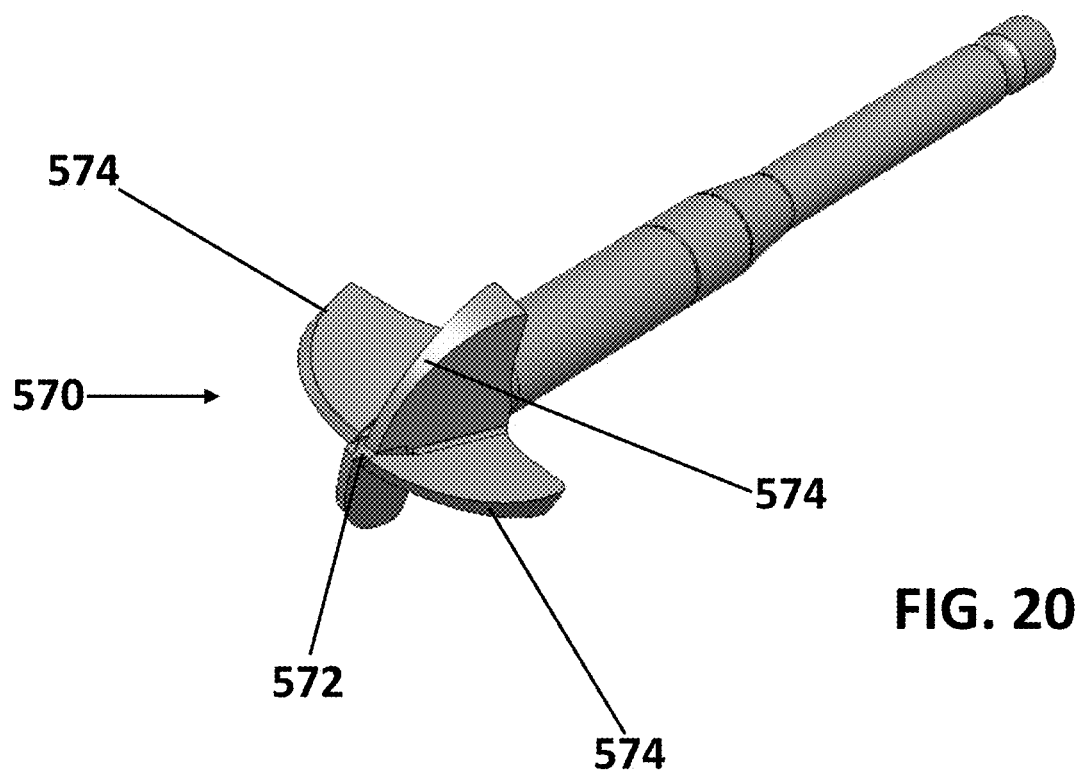
FIG. 20 is an orthographic view of a radial dish reamer tool in accordance with the present invention.

Optionally, the articular surface of the radius may be prepared to receive the radial component (100) by shaping the articular surface of the radius to match the external surface (132) of the dish (118) of the radial component (100). This is accomplished by using the optional radial dish reamer tool (570) shown in FIG. 20. The radial dish reamer tool orifice (572) is inserted over the k-wire placed in the previous step and the articular surface of the radius is then reamed until the cutting flutes (574) of the radial dish reamer tool (570) are flush with the radial edge of the articular surface of the radius. The k-wire can then be removed from the articular surface of the radius.

Figure 21:
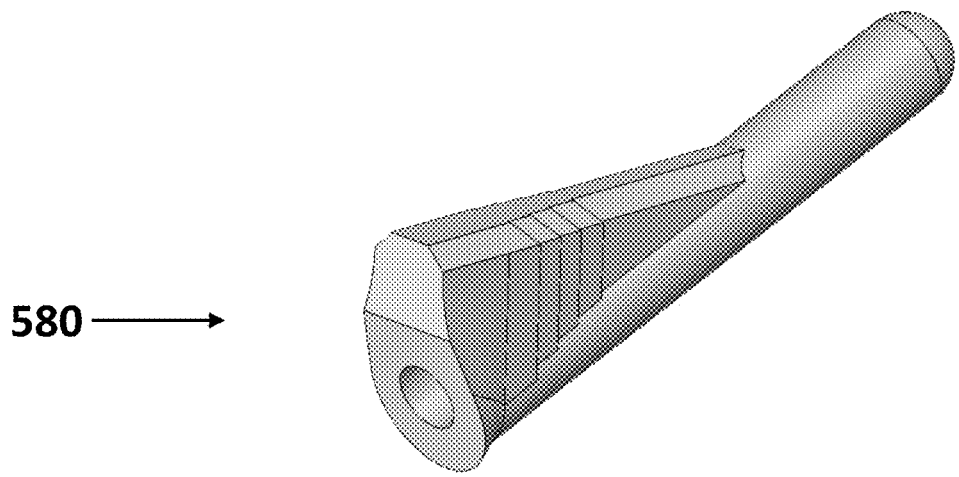
FIG. 21 is an orthographic view of a keel punch in accordance with the present invention.

The radial component (100) is then tapped into the radius with a surgical mallet until external surface (132) of the dish (118) of the radial component (100) makes full contact with the articular surface of the radius, further embedding stem (114) and keel (134) in the radius and locking the radial component in place. The articular surface of the radius may optionally be prepared for insertion of keel (134) by using optional keel punch (580) shown in FIG. 21. This step concludes the placement of the radial component (100).

Next, the long axis of the capitate bone is identified for placement of the carpal component (200). This may optionally be accomplished by using the capitate long axis guide (600) shown in FIG. 22. The guide (600) is placed on the third metacarpal bone and slid distally until ring (602) is flush with the proximate pole of the capitate bone. Next, a k-wire is inserted through orifice (604) of the guide and into the capitate bone. Guide (600) is then removed leaving the k-wire in place. Alignment of the k-wire may be confirmed using fluoroscopy.

As needed, the capitate bone may be shortened by using the optional stop reamer (620) shown in FIG. 23 over the k-wire inserted in the previous step. Next, the capitate bone is optionally prepared to receive the carpal component (200) by shaping the proximal articular surface of the capitate bone to match the internal surface (220) of cap (216) of the carpal component (200). This can be accomplished by using the optional capitate shaper (640) shown in FIG. 24. The orifice (642) of the capitate shaper (640), attached to a drill (not shown), is inserted over the k-wire placed in the previous step. The blades (644) are then used to shape the capitate bone to receive the carpal component (200).

Next, a first hole is drilled into the capitate using the previously inserted k-wire. The first hole is reamed to the appropriate size to accept the alignment pin (208) of the carpal component and the k-wire is removed.

A second hole is next drilled into the third metacarpal bone in longitudinal tangential alignment with the dorsal aspect of the capitate. The offset between the first and second holes matching the distance between the stem (204) and alignment pin (208) of the carpal component (200).

The alignment pin (208) and stem (204) of the carpal component (200) are then inserted into the first and second holes respectively until stem (204) is in the medullary canal of the third metacarpal bone and cap (216) makes contact with the capitate bone.

The carpal component is then tapped into the capitate bone with a surgical mallet until the capitate bone is fully encapsulated by cap (216). If the carpal component is equipped with optional wings (212H), and/or 212T), the wings should be positioned directly against the hamate and/or trapezoidal bones and can be secured using screws (251) through holes (213H, and/or 213T). Any gap between wings (212H, and/or 212T) and the hamate and/or trapezoidal bones may be filled with bone graft.

The lunate component (300) is next "snapped" onto the ball end (222) of the carpal component (200) through cavity (302) and the surgeon verifies that the carpal and lunate components are securely attached but freely swivel and rotate with respect to each other.

The external surface (301) of the lunate component is then buttressed against the dish (118) of the radial component (100) where it is allowed to "float." Again, the surgeon verifies that the lunate component (300) is free to rotate and swivel on the dish (118) of the radial component (100).

The surgeon then tests for correct operation of the prosthesis by manipulating and flexing the patient's hand through the range of natural wrist motion and observing proper alignment.

After any remaining alignment issues are corrected and satisfactory range of motion is achieved by the surgeon the incision is closed using standard surgical techniques.

Although described above connection with a prosthetic wrist, these descriptions are not intended to be limiting, as other prosthetic joints can be made in accordance with the description herein, and applied to different parts of the body such as elbows, shoulders, hips, knees and ankles. As such, although the invention is illustrated and described herein, various modifications and structural changes may be made therein without departing from the spirit of the invention and within the scope and range of equivalents of the claims.

We claim:

1. A wrist prosthesis comprising:
   a radial component having two sides, the first side comprising a stem and the second side comprising a concave dish;
   a carpal component having two sides, the first side comprising a stem, and the second side comprising a ball end, the ball end being connected to the carpal component through a neck, the neck being narrower than the diameter of the ball end; and
   a lunate component having two sides, the first side comprising a cavity adapted to receive said carpal component's ball end, and the second side comprising a convex surface adapted to engage said radial component's concave dish;
   said lunate component adapted to freely rotate with respect to at least one of said radial component and said carpal component about a longitudinal axis extending through the center of said ball end and substantially parallel to said stem of said carpal component.

2. A wrist prosthesis according to claim 1 wherein said stem of said carpal component is adapted for rigid engagement with one or more carpal and/or metacarpal bones.

3. A wrist prosthesis according to claim 1 wherein said stem of said radial component is adapted for rigid engagement with a radius bone.

4. A wrist prosthesis according to claim 1 wherein the lunate component further comprises a mouth connected to the cavity of the lunate component, the mouth being smaller in diameter than the diameter of the cavity.

5. A wrist prosthesis according to claim 1 wherein the ball end of the carpal component is adapted to snap into, and be retained by, the cavity of the lunate component.

6. A wrist prosthesis according to claim 5 wherein said lunate component comprises a resilient material.

7. A wrist prosthesis according to claim 1 wherein said carpal component further comprises an alignment pin substantially parallel to said stem of said carpal component.

8. A wrist prosthesis according to claim 7 wherein said alignment pin is adapted for rigid engagement to a capitate bone.

9. A wrist prosthesis according to claim 1 wherein said carpal component further comprises one or more wings, each positioned for anatomical alignment with an individual carpal bone.

10. A wrist prosthesis according to claim 9 wherein at least one of said wings comprises a fastener hole.

11. A wrist prosthesis according to claim 10 wherein said fastener hole is threaded.

12. A wrist prosthesis according to claim 1 wherein an axis extending along the length of the stem of said radial component is not normal to an imaginary line coplanar with edge of the concave dish of the radial component.

13. A wrist prosthesis according to claim 1 wherein an axis extending along the length of the stem of said radial component is approximately tangential to the concave dish of the radial component.

14. A method for surgically implanting a wrist prosthesis comprising the steps of:

rigidly engaging in the radius bone of a patient a radial component having two sides, the first side comprising a stem and the second side comprising a concave dish, by embedding said stem in said radius bone;

rigidly engaging in a carpal or metacarpal bone of a patient a carpal component having two sides, the first side comprising a stem, and the second side comprising a ball end, the ball end being connected to the carpal component through a neck, the neck being narrower than the diameter of the ball end, by embedding said stem in said carpal or metacarpal bone;

attaching to said carpal component's ball end a lunate component having a cavity adapted for such attachment; and engaging said lunate component with said concave dish of said radial component through a convex surface on said lunate component adapted for such engagement;

wherein said lunate component is adapted to freely rotate with respect to at least one of said radial component and said carpal component about a longitudinal axis extending through the center of said ball end and substantially parallel to said stem of said carpal component.

15. The method for surgically implanting a wrist prosthesis according to claim 14 wherein the lunate component further comprises a mouth connected to the cavity of the lunate component, the mouth being smaller in diameter than the diameter of the cavity.

16. The method for surgically implanting a wrist prosthesis according to claim 14 wherein the ball end of the carpal component is adapted to snap into, and be retained by, the cavity of the lunate component.

17. The method for surgically implanting a wrist prosthesis according to claim 16 wherein said lunate component comprises a resilient material.

* * * * *